United States Patent
Inoue (10) Patent No.: US 10,694,928 B2
(45) Date of Patent: Jun. 30, 2020

(54) ENDOSCOPE SYSTEM

(71) Applicant: OLYMPUS CORPORATION, Tokyo (JP)

(72) Inventor: Shintaro Inoue, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 346 days.

(21) Appl. No.: 15/820,746

(22) Filed: Nov. 22, 2017

(65) Prior Publication Data

US 2018/0132699 A1    May 17, 2018

Related U.S. Application Data

(63) Continuation of application No. PCT/JP2015/082096, filed on Nov. 16, 2015.
(Continued)

(51) Int. Cl.
*A61B 1/005* (2006.01)
*A61B 1/00* (2006.01)
(Continued)

(52) U.S. Cl.
CPC .......... *A61B 1/0052* (2013.01); *A61B 1/0005* (2013.01); *A61B 1/00006* (2013.01);
(Continued)

(58) Field of Classification Search
CPC ............ A61B 1/00006; A61B 1/00039; A61B 1/00045; A61B 1/00183; A61B 1/005;
(Continued)

(56) References Cited

U.S. PATENT DOCUMENTS 4,982,725 A * 1/1991 Hibino ............... A61B 1/00039
  600/104
5,469,840 A * 11/1995 Tanii ................... A61B 1/00039
  600/109
(Continued)

FOREIGN PATENT DOCUMENTS

EP   3 114 980 A1   1/2017
JP   H08-136832 A   5/1996
(Continued)

OTHER PUBLICATIONS

Chinese Office Action dated Nov. 29, 2018 in Chinese Patent Application No. 201580080444.3.
(Continued)

*Primary Examiner* — Aaron B Fairchild
(74) *Attorney, Agent, or Firm* — Scully, Scott, Murphy & Presser, P.C.

(57) ABSTRACT

An endoscope system includes: an insertion part having a bending part; an observation unit; an operation unit configured to operate the bending part; a driving mechanism configured to generate a driving force used to drive the bending part; a control unit configured to control the driving mechanism; and a display unit configured to display a visual field image acquired by the observation unit, wherein the control unit has a normal mode and a lock-on mode as control modes, and the control unit is configured to stop an automatic driving of the bending part temporarily and allow the operation unit to perform a resetting of an interested position when an output from the operation unit exceeds a predetermined threshold value, and resume the automatic driving on the basis of the updated interested position when an output from the operation unit satisfies a predetermined termination condition during the lock-on mode.

6 Claims, 7 Drawing Sheets

Related U.S. Application Data (60) Provisional application No. 62/167,424, filed on May 28, 2015.

(51) Int. Cl.
  *A61B 1/05* (2006.01)
  *A61B 1/313* (2006.01)
  *A61B 17/34* (2006.01)
  *A61B 34/20* (2016.01)
  *A61B 90/00* (2016.01)
  *H04N 5/225* (2006.01)

(52) U.S. Cl.
  CPC ...... *A61B 1/00009* (2013.01); *A61B 1/00039* (2013.01); *A61B 1/00045* (2013.01); *A61B 1/00183* (2013.01); *A61B 1/05* (2013.01); *A61B 1/3132* (2013.01); *A61B 17/3423* (2013.01); *A61B 2034/2059* (2016.02); *A61B 2090/061* (2016.02); *A61B 2090/0811* (2016.02); *A61B 2090/373* (2016.02); *H04N 2005/2255* (2013.01)

(58) Field of Classification Search
  CPC ....... A61B 1/0052; A61B 1/05; A61B 1/3132; A61B 17/3498; A61B 1/0051; A61B 1/0058; A61B 1/01
  See application file for complete search history.

(56) References Cited

U.S. PATENT DOCUMENTS

| | | | | |
|---|---|---|---|---|
| 5,658,238 A | * | 8/1997 | Suzuki | A61B 1/00039 600/146 |
| 2002/0156345 A1 | | 10/2002 | Eppler et al. | |
| 2004/0073083 A1 | * | 4/2004 | Ikeda | A61B 1/00039 600/101 |
| 2007/0015967 A1 | * | 1/2007 | Boulais | A61B 1/0005 600/146 |
| 2007/0173694 A1 | * | 7/2007 | Tsuji | A61B 1/0005 600/146 |

FOREIGN PATENT DOCUMENTS

| | | |
|---|---|---|
| JP | H10309256 A | 11/1998 |
| JP | H11104064 A | 4/1999 |
| JP | 2000271081 A | 10/2000 |
| JP | 2011036460 A | 2/2011 |
| WO | 2015/012082 A1 | 1/2015 |

OTHER PUBLICATIONS

Extended Supplementary European Search Report dated Dec. 12, 2018 in European Patent Application No. 15 89 3397.8.
International Search Report dated Feb. 9, 2016 issued in PCT/JP2015/082096.

\* cited by examiner

ENDOSCOPE SYSTEM

This application is a continuation application based on PCT Patent Application No. PCT/JP2015/082096, filed Nov. 16, 2015, claiming priority based on U.S. Provisional Application No. 62/167,424, filed May 28, 2015, the content of which is incorporated herein by reference.

BACKGROUND OF THE INVENTION

Field of the Invention

The present invention relates to an endoscope system.

Description of the Related Art

In the related art, techniques of introducing observation tools such as laparoscopes and treatment tools into patient's bodies and performing various treatments are known. The observation tools function as eyes of operators performing treatments. Therefore, when a target portion to be treated or the treatment tool goes out of a visual field of the observation tool due to unintentional movements or the like of the observation tool, it is difficult to continue treatment.

With regard to this problem, Japanese Unexamined Patent Application, First Publication No. H10-309256 proposes an endoscope apparatus driving to keep capturing a treatment tool in its visual field. In the endoscope apparatus of Japanese Unexamined Patent Application, First Publication No. H10-309256, the endoscope apparatus recognizes a marker provided at a distal end of the treatment tool and is driven so that a virtual point on an image displayed on a monitor coincides with the marker.

Solution to Problem

According to one aspect of the present invention, an endoscope system including: an insertion part having a bending part capable of being bent; an observation unit provided at a distal end portion of the insertion part; an operation unit configured to operate the bending part; a driving mechanism configured to generate a driving force used to drive the bending part; a control unit configured to control the driving mechanism; and a display unit configured to display a visual field image acquired by the observation unit, wherein the control unit has a normal mode of driving the bending part in accordance with an output from the operation unit and a lock-on mode that performs an automatic driving of the bending part such that the observation unit faces a predetermined interested position irrespective of the output as control modes, and the control unit is configured to stop the automatic driving temporarily and allow the operation unit to perform a resetting of the interested position when an output from the operation unit exceeds a predetermined threshold value, and resume the automatic driving on the basis of the updated interested position when an output from the operation unit satisfies a predetermined termination condition during the lock-on mode.

The control unit may be configured to drive the bending part in accordance with an output from the operation unit when the control unit allows the resetting. Alternatively, the control unit may be configured to display a cursor in the visual field image displayed on the display unit and move the cursor in the visual field image in accordance with an output from the operation unit.

The control unit may be configured to update the interested position when an output from the operation unit satisfies the predetermined termination condition after the control unit allows the resetting.

The operation unit may be configured to be capable of moving a position to be designated as the interested position in a depth direction of the visual field image during the resetting is allowed.

Advantageous Effects of Invention

According to the endoscope system of the present invention, an interested position is capable of being easily reset.

DETAILED DESCRIPTION OF THE PREFERRED EMBODIMENTS

Figure 1:
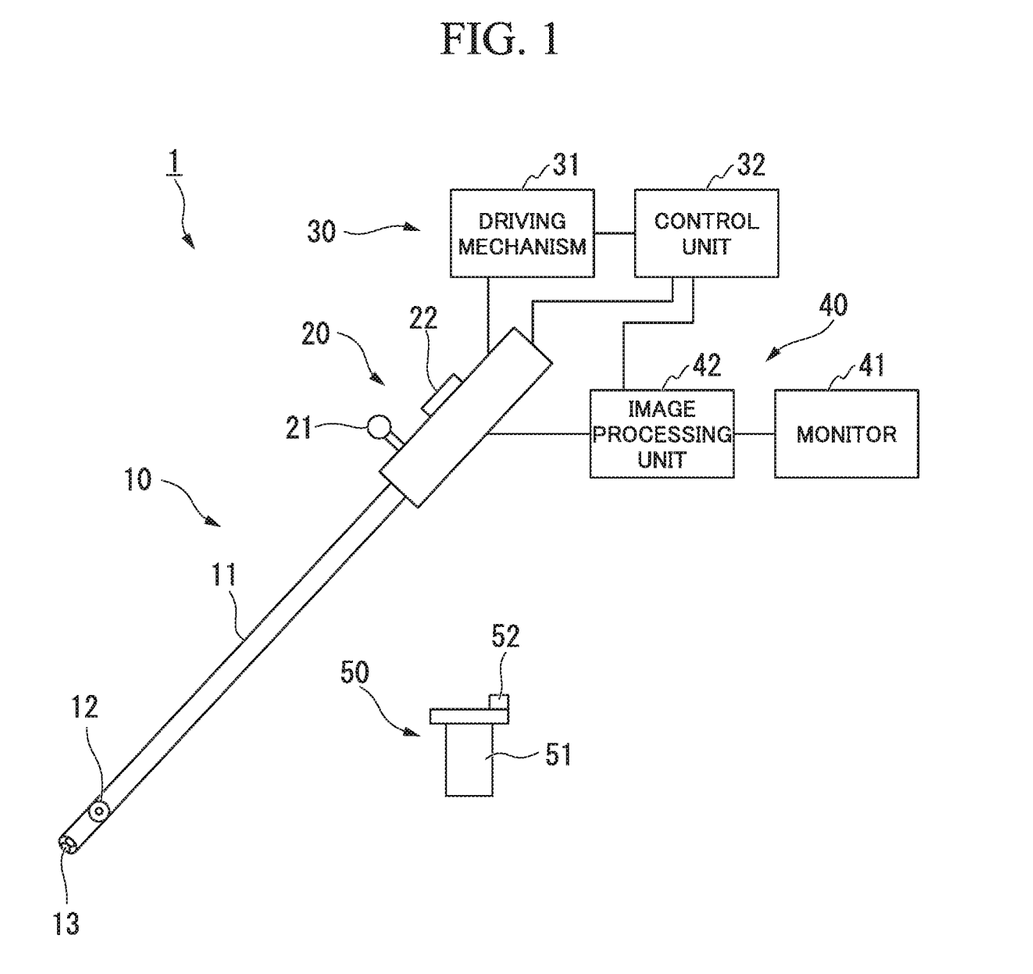
FIG. 1 is a diagram showing the overall constitution of an endoscope system according to a first embodiment of the present invention.
Figure 2:
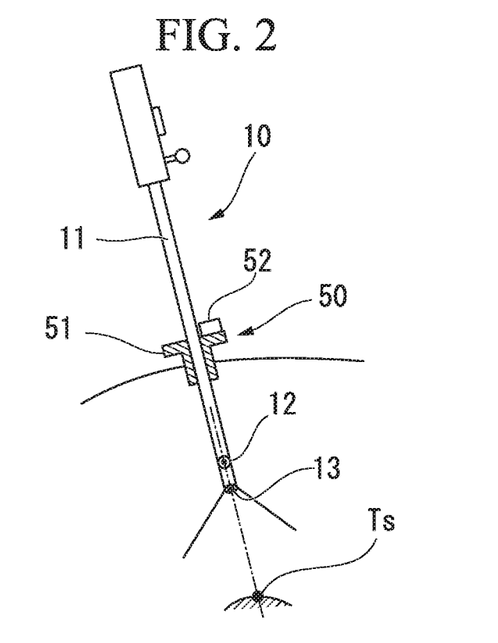
FIG. 2 is a diagram showing a behavior of an endoscope in a lock-on mode.
Figure 3:
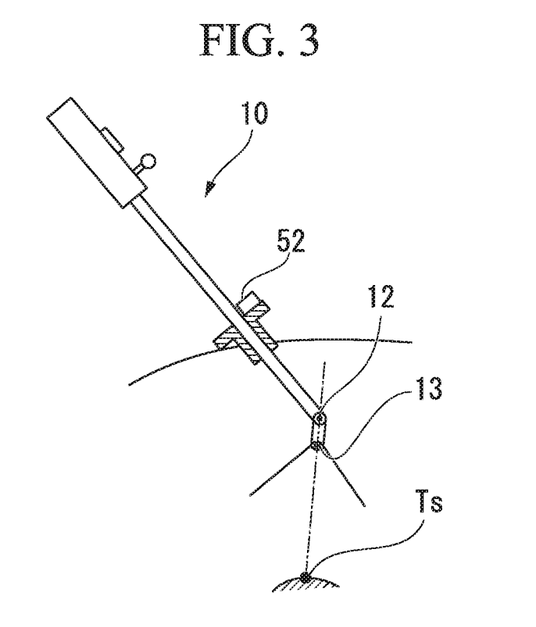
FIG. 3 is a diagram showing a behavior of an endoscope in a lock-on mode.

A first embodiment of the present invention will be described with reference to FIGS. 1 to 4. FIG. 1 is a diagram showing the overall constitution of an endoscope system 1 according to the embodiment. The endoscope system 1 includes an endoscope 10 inserted into a patient's body and a trocar 50 which is held in the patient's body wall and into which the endoscope 10 is inserted.

The endoscope 10 includes an elongated insertion part 11, an operation unit 20, a driving unit 30, and a display unit 40.

The insertion part 11 has a bending part 12 capable of being bent at a distal end portion thereof. A specific structure of the bending part 12 is not particularly limited. Therefore, a known joint structure having one or more joints with an axis of rotation, a known bending tube structure having a plurality of joint rings or bending pieces (hereinafter referred to as "joint rings or the like"), or the like is capable of being appropriately selected and adopted. An encoder or the like (not shown) is attached to the bending part 12, and the bending part 12 is configured to be capable of detecting the amount of rotation of each joint in a joint structure or the amount of turning of each joint ring or the like.

An observation unit 13 including an imaging device, a lighting mechanism, or the like is provided at the distal end portion of the insertion part 11. The observation unit 13 is provided at a further distal end side than the bending part 12. With regard to the observation unit 13, a structure of an observation tool in a known endoscope is also capable of being appropriately selected and adopted. The observation unit 13 has a distance measurement function used to measure the distance to an object captured in a visual field. As a mechanism for realizing the distance measurement function, a known mechanism of a stereo measurement or the like is capable of being appropriately selected and adopted.

The operation unit 20 includes a joystick 21 and a button 22. When a user operates the joystick 21, an operation output is transferred to the driving unit 30 and the bending part 12 is driven. As a result, the observation unit 13 is capable of being directed in a desired direction. The button 22 is used for switching a driving mode of the endoscope 10. Details of the driving mode will be described below.

The driving unit 30 includes a driving mechanism 31 configured to generate a driving force used to drive the bending part 12 and a control unit 32 configured to control an operation of the driving mechanism 31. Various known motors or the like are capable of being used as the driving mechanism 31. The driving mechanism 31 and the bending part 12 are connected through a transmission member such as a wire (not shown). The bending part 12 is driven by transferring the driving force generated by the driving mechanism 31 to the bending part 12 via the transmission member.

An arrangement position of the driving mechanism 31 is not particularly limited. For example, the driving mechanism 31 may be arranged in an operation unit and may be provided at a position away from an operation unit by extending the transmission member or the like.

The control unit 32 is electrically connected to the operation unit 20 and the driving mechanism 31. The control unit 32 generates a driving signal used to drive the driving mechanism 31 and transmits the generated driving signal to the driving mechanism 31. Although a mode of generating the driving signal differs depending on a driving mode, the details thereof will be described below.

The display unit 40 includes a monitor 41 and an image processing unit 42. A video signal acquired by the observation unit 13 is sent to the image processing unit 42. After the video signal is processed by the image processing unit 42, the processed video signal is displayed on the monitor 41. As the display unit 40, a display mechanism of a known endoscope system is capable of being appropriately selected and used.

The control unit 32 and the image processing unit 42 are electrically connected. Therefore, the operation unit 20 also functions as an interface configured to operate a cursor or the like displayed on the monitor 41.

The trocar 50 includes a tubular main body 51 and a sensor 52 attached to the main body 51.

A basic structure of the main body 51 is the same as a known trocar and the insertion part 11 of the endoscope 10 is capable of being inserted into the main body 51. The main body 51 may include a valve configured to maintain a pneumoperitoneum state or an inner needle configured to pierce a body wall or the like as necessary.

The sensor 52 is capable of detecting the amount of advancement and retraction of the insertion part 11 inserted into the trocar 50, the amount of rotation around an axis of the insertion part 11, and an orientation (substantially the same as a direction of the axis of the insertion part 11 inserted into the trocar 50) of the main body 51. The sensor 52 is capable of being constituted using a known encoder or the like. An auxiliary structure configured to enable or facilitate detection of various amounts of operations of the insertion part 11 using the sensor 52 may be provided in the insertion part 11 as necessary.

The sensor 52 is configured to be capable of transmitting and receiving information to and from the control unit 32, and a detection value of the sensor 52 is sent to the control unit 32.

An operation of the endoscope system 1 according to the embodiment configured as described above in use will be described.

A user makes a hole in a body wall such as a patient's abdominal wall, inserts the trocar 50 through the hole, and holds the trocar 50 on the body wall. After that, the user inserts the endoscope 10 from the observation unit 13 side into the trocar 50 and introduces the observation unit 13 and the bending part 12 into the patient's body. A video acquired by the observation unit 13 in the body is displayed on the monitor 41 of the display unit 40.

The endoscope system 1 has two operation modes, i.e., a manual mode (a normal mode) and a lock-on mode.

In the manual mode, the control unit 32 generates a driving signal on the basis of an operation of the joystick 21 by the user and transmits the generated driving signal to the driving mechanism 31. As a result, the bending part 12 is bent in response to the operation of the joystick 21.

In the lock-on mode, the control unit 32 automatically generates a driving signal such that the observation unit 13 faces coordinates (an interested position) set by the user at all times and transmits the generated driving signal to the driving mechanism 31. Therefore, for example, when the user moves the endoscope 10 from the state shown in FIG. 2 to the state shown in FIG. 3, the bending part 12 is driven such that the observation unit 13 faces an interested position Ts even after being moved. In other words, during the lock-on mode, the bending part 12 is automatically driven by the control unit 32 such that the observation unit 13 faces the interested position Ts no matter how the user moves the endoscope 10. During the lock-on mode, the interested position Ts is controlled to be located at a predetermined position (for example, a center) of a visual field image displayed on the monitor 41 at all times.

An initial setting of the interested position Ts is performed, for example, as follows.

When the user sets one point of a visual field video displayed on the monitor 41 as an interested position, the control unit 32 sets coordinates of the interested position Ts on the basis of a positional relationship between the insertion part 11 and the trocar 50 and an orientation of the main body 51 received from the sensor 52, a bending state of the bending part 12 received from the bending part 12, the distance between the observation unit 13 and the interested position Ts, or the like. After that, whenever the insertion part 11 is advanced and retracted or rotated with respect to the trocar 50, the amount of operation of the insertion part 11 with respect to the trocar 50 and the orientation of the main body 51 detected by the sensor 52 are transmitted to the control unit 32. The control unit 32 calculates the amount of operation of the bending part 12 required for causing the observation unit 13 to face the interested position Ts again on the basis of the amount of operation of the insertion part 11 and the orientation of the main body 51 received from the sensor 52, and a current bending state of the bending part 12. Then, the control unit 32 generates a driving signal so that the bending part 12 is driven by the required amount of operation, and sends the generated driving signal to the driving mechanism 31. As a result, the bending part 12 is automatically driven by the driving mechanism 31 and the observation unit 13 faces the interested position.

Transition between the manual mode and the lock-on mode is performed by the button 22. In other words, when the button 22 is pressed, switching is performed from the manual mode to the lock-on mode or from the lock-on mode to the manual mode. Since the bending part 12 is automatically driven by the control unit 32 during the lock-on mode, outputs from the joystick 21 based on operations of the user are all cancelled at the control unit 32 except for a predetermined case which will be described below and are not used for driving the bending part 12.

In the endoscope system 1, an interested position is capable of being easily reset during a lock-on mode. A procedure of resetting the interested position will be described below.

Figure 4:
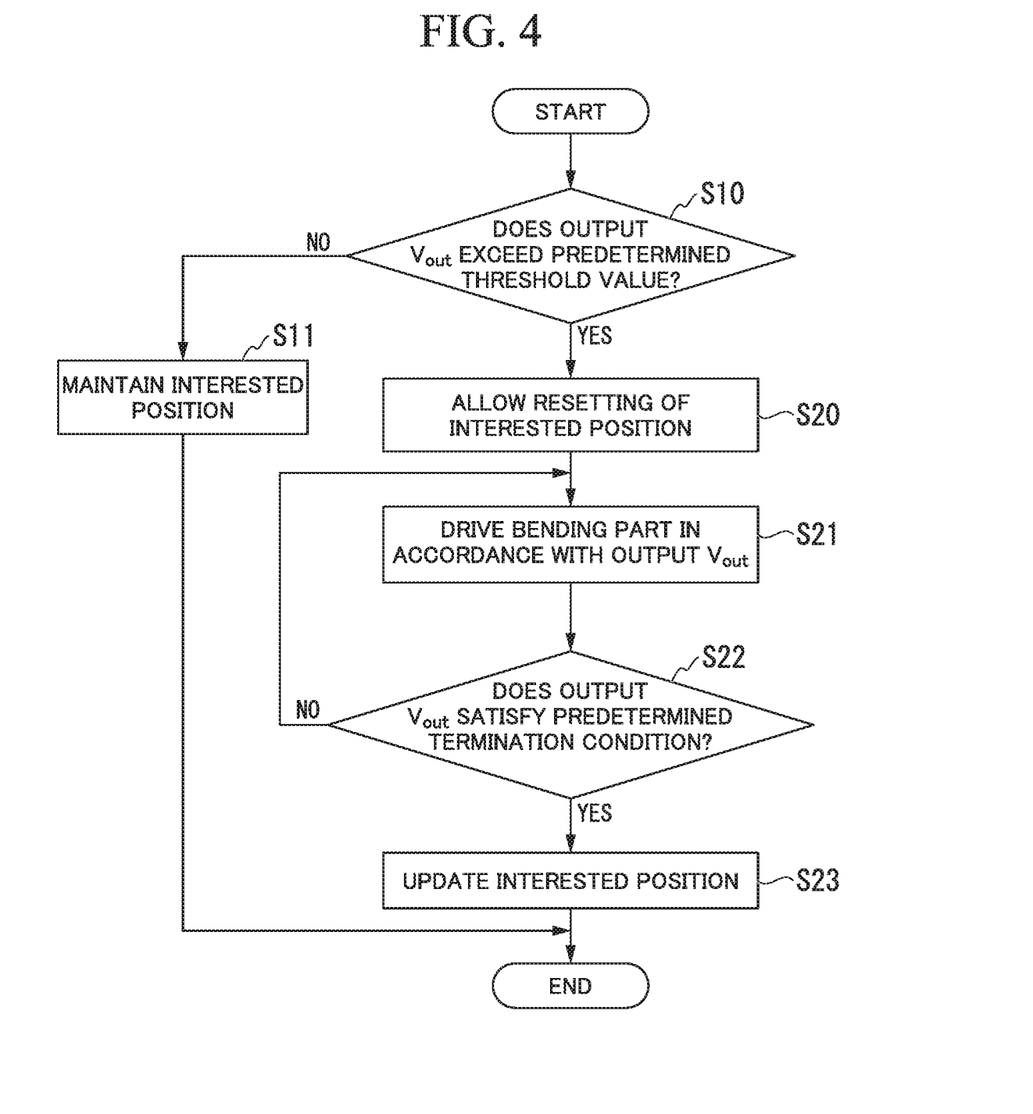
FIG. 4 is a flowchart showing a flow of resetting of an interested position in a lock-on mode of the endoscope system.

FIG. 4 is a flowchart showing an operational flow associated with resetting of an interested position of the endoscope system 1 during a lock-on mode. Such a flow is repeatedly performed during a lock-on mode.

In Step S10, the control unit 32 determines whether an output $V_{out}$ from the joystick 21 exceeds a predetermined threshold value. When the determination result is No, the process proceeds to a process of Step S11, the interested position is maintained, and the flow ends.

When the determination result is Yes, the process proceeds to a process of Step S20. In Step S20, the control unit 32 temporarily stops the automatic driving of the bending part 12 and allows the resetting of the interested position.

The above-described predetermined threshold value is capable of being appropriately set. For example, in a case of a constitution in which an operation output (a voltage value or a current value) changes continuously in accordance with the amount of tilting of the joystick 21, an operation output value when the joystick 21 is tilted by a predetermined amount may be set as a threshold value. Furthermore, in a case of a constitution in which an operation output is constant irrespective of the amount of tilting of the joystick 21 and the operation output is either ON or OFF, a threshold value may be set to the duration of a state in which the operation output is ON. In any case, by appropriately setting a threshold value, the endoscope system 1 is capable of being suitably prevented from entering the resetting state of the interested position due to, for example, the unintentional touching to the joystick 21 by the user or the like.

In Step S21 subsequent to Step S20, the control unit 32 generates a driving signal according to the output $V_{out}$ and drives the driving mechanism 31. As a result, the bending part 12 is driven in substantially the same manner as in the manual mode and a visual field of the observation unit 13 changes. The user moves a portion she or he desires to set to a new interested position at a center of a visual field image while changing the visual field of the observation unit 13.

In Step S22 subsequent to Step S21, the control unit 32 determines whether the output $V_{out}$ satisfies a predetermined termination condition. As an exemplary example of the termination condition, for example, a case in which a state in which the output $V_{out}$ is zero continues for a predetermined length (for example, two seconds) may be used.

When the determination result of Step S22 is No, the process returns to the process of Step S21. When the determination result is Yes, the process proceeds to a process of Step S23.

In Step S23, the control unit 32 measures the distance between an object located at the center of the visual field and the observation unit 13, calculates coordinates of the object in the same procedure as in the initial setting of the interested position, and updates the interested position. Subsequently, the flow ends. After the flow ends, the control unit 32 resumes the automatic driving of the bending part 12 on the basis of the updated interested position.

As described above, according to the endoscope system 1 of the embodiment, when it is necessary to reset an interested position during a lock-on mode, the control unit 32 allows the resetting of the interested position using the operation unit 20 when the operation unit 20 is operated so that an output from the operation unit 20 exceeds a predetermined threshold value. Therefore, there is no need to end the lock-on mode by operating the button 22 to reset the interested position. In other words, after resetting the interested position using the operation unit 20, the automatic driving of the bending part 12 targeted for the updated interested position is promptly resumed by the control unit 32.

As a result, the interested position is capable of being easily reset during the lock-on mode and thus the interruption of a procedure due to the resetting is capable of being reduced.

The allowance of the resetting and the end determination of the resetting of the interested position by the control unit 32 are both performed on the basis of an output mode from the joystick 21. Therefore, the user is capable of resetting the interested position by operating only the joystick 21 and it is not necessary to operate both the joystick 21 and the button 22.

A second embodiment of the present invention will be described below with reference to FIGS. 5 to 7. The difference between an endoscope system according to this embodiment and the above-described endoscope system 1 is a behavior at a time of resetting an interested position. In the following description, the same constituent elements as those already described will be denoted with the same reference numerals and a repeated description thereof will be omitted.

Figure 5:
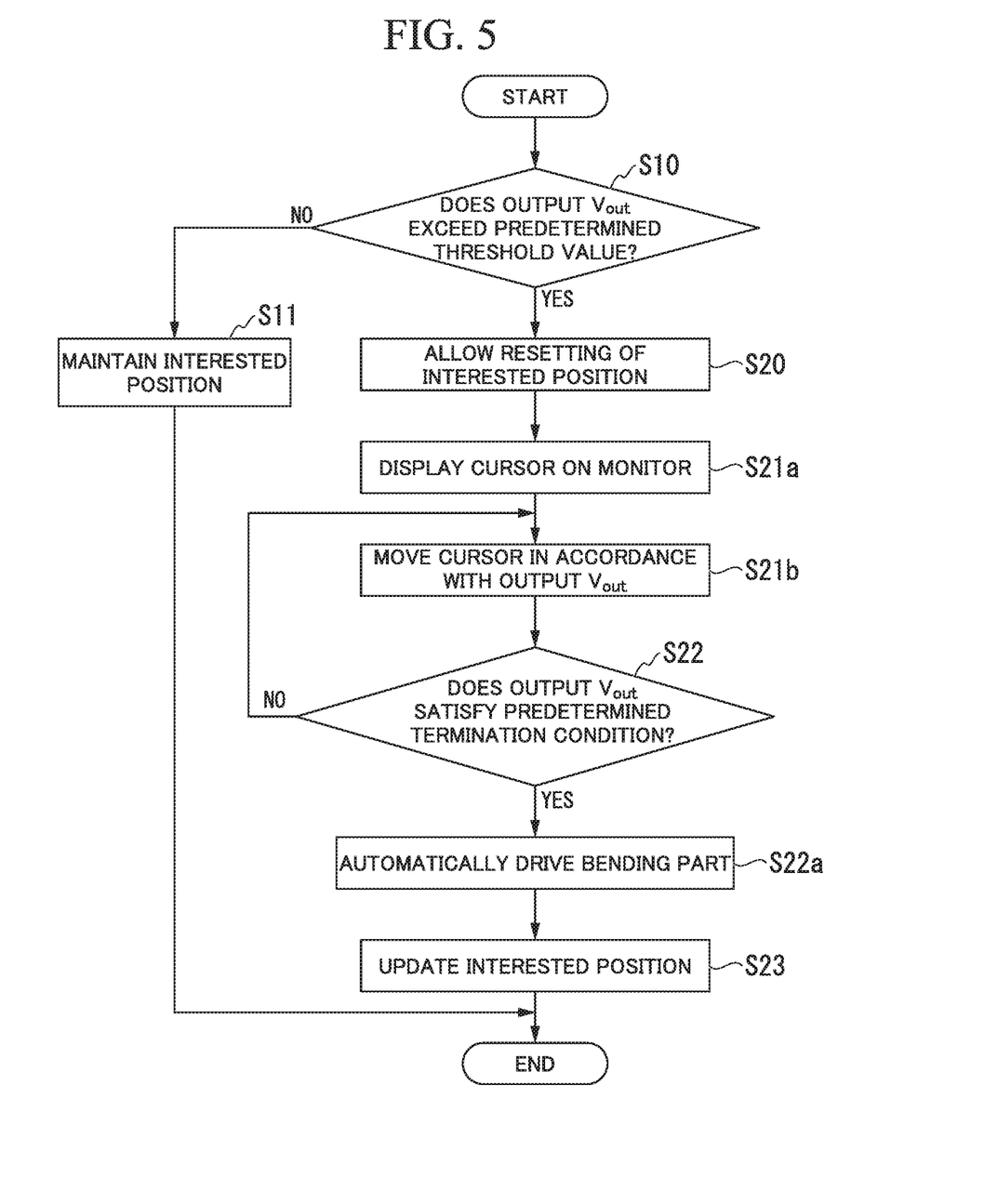
FIG. 5 is a flowchart showing a flow of resetting of an interested position in a lock-on mode of an endoscope system according to a second embodiment of the present invention.

FIG. 5 is a flowchart showing an operational flow associated with resetting of an interested position during a lock-on mode in the endoscope system according to this embodiment. In this embodiment, in Step S20, the control unit 32 allows the resetting of the interested position and then the process proceeds to a process of Step S21a.

Figure 6:
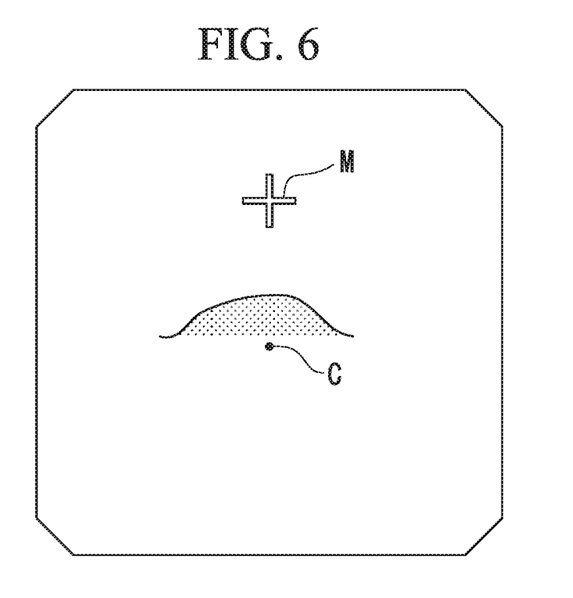
FIG. 6 is an example of a visual field image of the endoscope system at the time of resetting of an interested position.
Figure 7:
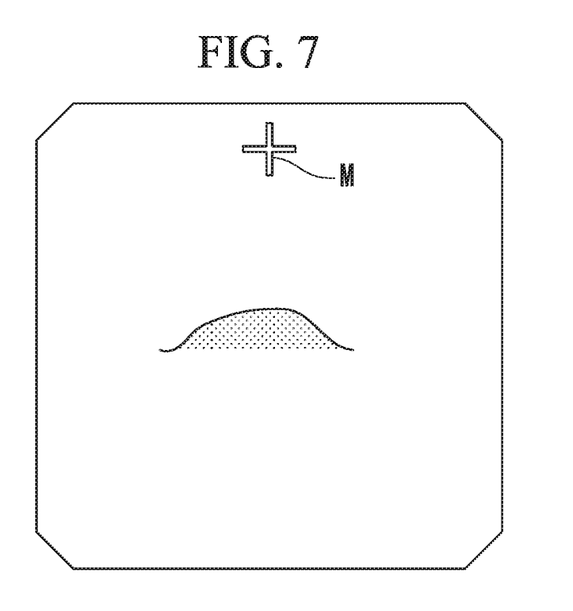
FIG. 7 is an example of a visual field image in a modified example of the endoscope system.

As shown in FIG. 6, in Step S21a, the control unit 32 controls the display unit 40 to display a cursor M for resetting of the interested position at a center of a visual field image displayed on the monitor 41.

Subsequently, in Step S21b, the control unit 32 moves the cursor M in the visual field image in accordance with the output $V_{out}$ from the joystick 21. In Step S21a, since the bending part 12 is not driven, the visual field image displayed on the monitor 41 does not change.

When the user moves the cursor to a desired position and the determination result of Step S22 is Yes, the process proceeds to a process of Step S22a.

In Step S22a, the control unit 32 calculates the amount of driving of the bending part 12 required for moving a portion of an object overlapping the cursor M to a center C of the visual field image on the basis of the distance between the center C of the visual field image and the cursor M. Then, the control unit 32 generates a driving signal, and sends the generated driving signal to the driving mechanism 31. As a result, the bending part 12 is automatically driven, and the cursor M and the object overlapping the cursor M are moved to the center C of the visual field image.

Subsequently, in Step S23, the distance between the object located at the center C of the visual field image and the observation unit 13 is measured and the interested position is updated. Then, the flow ends.

Also in the endoscope system according to this embodiment, similarly to the endoscope system 1 according to the first embodiment, the interested position is capable of being easily reset during the lock-on mode and thus the interruption of the procedure due to the resetting is capable of being reduced.

In this embodiment, since the bending part 12 is not driven during the resetting of the interested position, the visual field image displayed on the monitor 41 does not change. Therefore, it is unlikely that a situation such as a portion desired to be set to a new interested position moves outside of a visual field of the endoscope 10 due to large movement of the visual field by an operation mistake or the like during the resetting by the user will occur.

In this embodiment, when the interested position is updated, a bending part may not necessarily be automatically driven. For example, when an endoscope is configured so that the distance between an object located at any point in a visual field image and an observation unit is capable of being measured by a known stereo measurement or the like, coordinates of the object at a position of the cursor M may be identified in Step S22a and the interested position may be updated. In this case, a process of updating the interested position is capable of being quickly performed without changing the visual field image.

As a modified example of this embodiment, the bending part 12 may be driven under a predetermined condition during the resetting of the interested position. For example, as shown in FIG. 7, a system may be configured such that the control unit 32 drives the bending part 12 so that the visual field of the observation unit 13 moves in a moving direction of the cursor M and the control unit 32 performs control so that the cursor M does not move outside of the visual field image when the output $V_{out}$ is still detected even when the cursor M moves to an end of the visual field image.

A third embodiment of the present invention will be described below with reference to FIGS. 8 to 10. An endoscope system 101 according to this embodiment and the endoscope systems according to the above-described embodiments differ in that the endoscope system 101 is capable of performing fine adjustment of coordinates of an interested position at the time of resetting.

Figure 8:
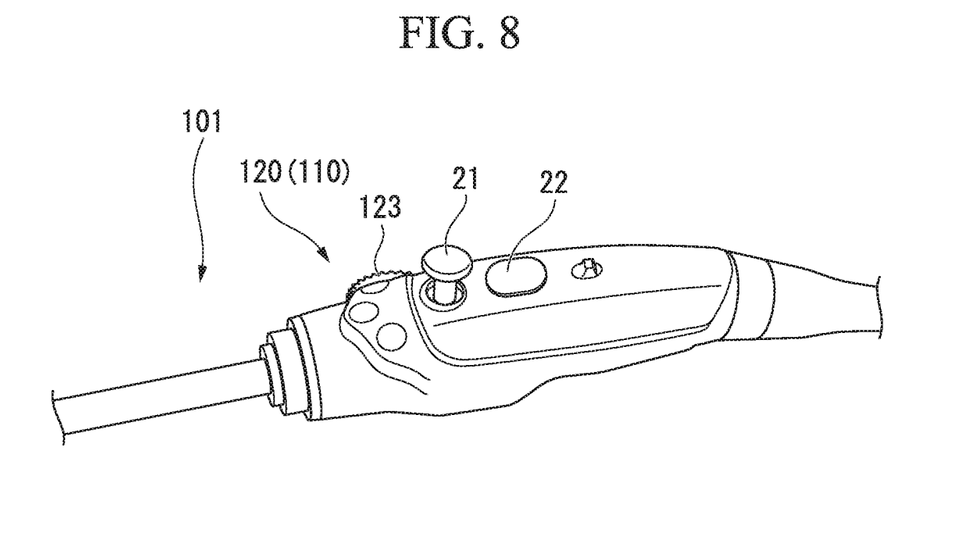
FIG. 8 is an enlarged view showing an operation unit of an endoscope system according to a third embodiment of the present invention.

FIG. 8 is a diagram showing an operation unit 120 of an endoscope 110 in the endoscope system 101. A wheel 123 is rotatably attached to the operation unit 120. The rotational direction and the amount of rotation of the wheel 123 are detected by an encoder or the like (not shown) and sent to the control unit 32.

An operation flow at the time of resetting an interested position in the endoscope system 101 is basically the same as that in the second embodiment. In other words, the user designates a portion that she or he desires to set as a new interested position by operating a cursor displayed on the monitor 41 using the operation unit 120. At this time, the user moves the cursor to a desired position in a visual field image using the joystick 21 and performs fine adjustment for the portion that she or he desires to set as the interested position by operating the wheel 123 as necessary.

Fine adjustment using the wheel 123 will be described. By operating the wheel 123, a desired value is capable of being added to or subtracted from a value of the distance (a distance value) between the observation unit 13 and the interested position used when the control unit 32 resets the interested position.

Figure 9:
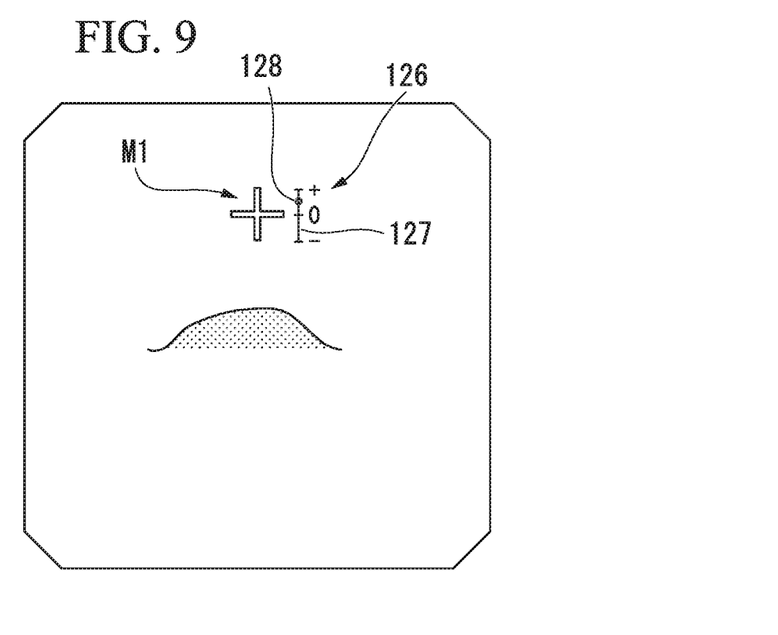
FIG. 9 is an example of a visual field image of the endoscope system at the time of resetting of an interested position.

FIG. 9 shows a cursor M1 in this embodiment. The cursor M1 includes an indicator 126 indicating an adjustment value for the value of the distance. The indicator 126 includes a bar 127 and a marker 128 displayed on the bar 127. When the marker 128 is located at a midpoint of the bar 127, the adjustment value is zero. When the user rotates the wheel 123 toward the insertion part 11, the marker 128 moves to an upper side of the bar 127. When the user rotates the wheel 123 toward a hand side, the marker 128 moves to a lower side of the bar 127. When the marker 128 is located above the midpoint of the bar 127, the adjustment value is positive and when the marker 128 is located below the midpoint thereof, the adjustment value is negative. An absolute value of the adjustment value increases as the marker 128 is farther from the midpoint of the bar 127.

In this embodiment, when the interested position is reset in Step S23, the control unit 32 refers to detection values associated with the rotational direction and the amount of rotation of the wheel 123.

When the amount of rotation is zero, the control unit 32 updates the interested position in the same procedure as in the second embodiment. When the amount of rotation is not zero, the control unit 32 determines the adjustment value on the basis of the rotational direction and the amount of rotation. Subsequently, a measurement value of the distance between an object located at a center of the visual field image and the observation unit 13 is adjusted using the adjustment value. In other words, when the adjustment value is positive, coordinates of a new interested position are calculated after adding the adjustment value to the measurement value, and when the adjustment value is negative, coordinates of a new interested position are calculated after subtracting the adjustment value from the measurement value.

The other points are similar to those of the second embodiment.

Also in the endoscope system 101 according to this embodiment, similarly to the above-described embodiments, the interested position is capable of being easily reset during the lock-on mode and thus the interruption of the procedure due to the resetting is capable of being reduced.

Also, as an effect unique to this embodiment, coordinates of a portion to be designated as a new interested position at the time of resetting the interested position are capable of being finely adjusted. Thus, the portion to be designated as the new interested position is capable of being designated not only on a visual field image but also on a location moved in a depth direction of the visual field image.

Figure 10:
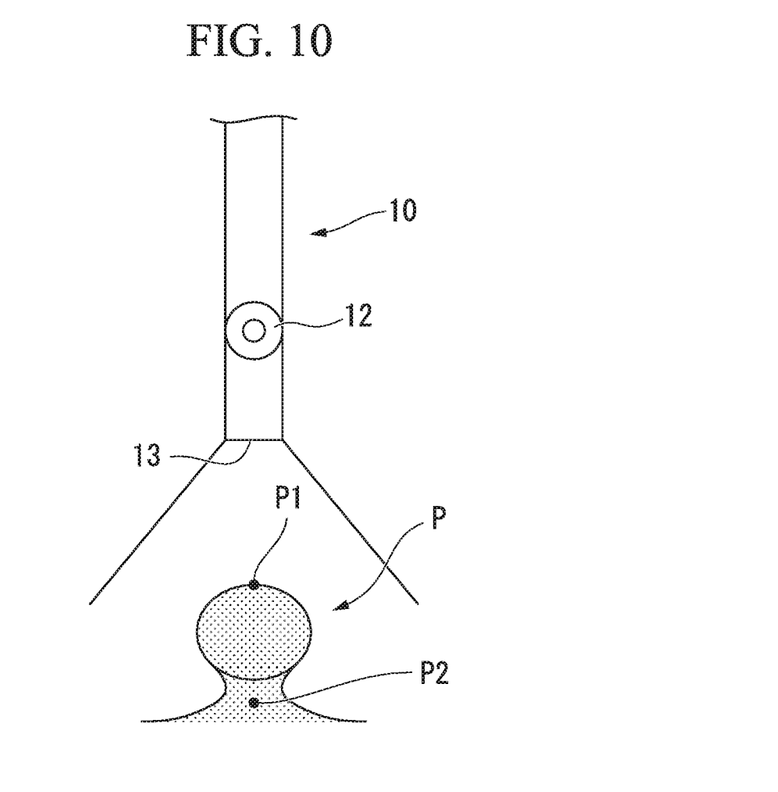
FIG. 10 is a diagram showing an example of a relationship between an object and an interested position to be set.

For example, when it is desired to observe a polyp P as shown in FIG. 10 in a lock-on mode, the polyp P is set as an interested position in a state in which the polyp P is observed using the endoscope 10 from directly above. Thus, coordinates of the interested position are set at an apex P1 of the polyp P. Here, when the observation unit 13 is moved to the side of the polyp P to attempt to observe the polyp P from the side thereof, the bending part 12 is automatically driven such that the observation unit 13 faces the apex P1. Therefore, when a portion desired to be actually observed is a base part P2 or the like of the polyp P, the portion desired to be observed is likely to move outside of a visual field even during the lock-on mode.

In this embodiment, since a distance value used for calculating coordinates of a new interested position is adjusted to increase or decrease by operating the wheel 123, the interested position is capable of being set not only on a surface of an object located in the visual field image but also on a far side or a near side thereof. For example, when adjustment is made to increase the distance value, the vicinity of the base part P2 is capable of being designated as a new interested position even when the polyp P is observed from directly above.

In this embodiment, a constitution of an indicator is not limited to the above-described constitution. For example, a positive adjustment value and a negative adjustment value are displayed in a warm color system such as red or orange and a cold color system such as blue or purple, respectively, and the color becomes darker as an absolute value of the adjustment value increases so that the adjustment value may be indicated only by the color. Alternatively, the adjustment value itself may be configured to be displayed using signed numbers with positive and negative signs.

A mechanism of an operation unit configured to designate an adjustment value is not limited to the above-described wheel either. For example, a joystick may be configured to be pushed in and pulled out in an axial direction thereof, and may be configured to designate the adjustment value according to pushing and pulling of the joystick.

In addition, a system may be configured so that a distance value is capable of being adjusted in one of positive and negative values.

Although the embodiments of the present invention have been described above, the technical scope of the present invention is not limited to the above-described embodiments and it is possible to change a combination of constituent elements, variously modify constituent elements, or delete constituent elements without departing from the gist of the present invention.

For example, in the endoscope system of the present invention, a mode of automatic driving in a lock-on mode is not limited to a mode in which an observation unit faces predetermined coordinates set as an interested position.

Examples of a mode of automatic driving include a mode of causing an observation unit to face an interested position by setting a desired point in a visual field image together with feature point information for identification as the interested position and automatically driving a bending part such that the interested position is located at a center of the visual field image at all times. In this case, since it is not necessary to calculate coordinates of the interested position, but an external appearance of the point in the visual field image changes due to a change in observation direction in some cases, a system is preferably configured such that a control unit performs automatic driving while updating feature point information as needed.

Also, although a case in which a position of an observation unit at a distal end of an endoscope is identified using information of a sensor provided in a trocar has been described in the above-described embodiments, the position of the observation unit may be identified using other information. For example, an optical marker may be attached to a portion of an endoscope located outside a body, a position of a predetermined portion of the endoscope may be identified by a known technique using the optical marker, and a position of an observation unit may be identified using position information of the predetermined portion. Alternatively, an endoscope may be held by an arm or the like installed outside a body and the position of an observation unit may be identified using position information of a predetermined portion acquired on the basis of a joint angle or the like of the arm.

Although a description has been provided using a so-called rigid endoscope in which an insertion part does not have flexibility as an example in the above-described embodiments, a so-called flexible endoscope in which an insertion part has flexibility may be used. In this case, for example, a plurality of magnetic sensors or the like are arranged in the insertion part and a shape of the insertion part in a body is identified using a known technique. Moreover, a position of an observation unit may be identified by combining the identified shape information of the insertion part.

In addition, a position in a visual field image in which an interested position is displayed in a lock-on mode is not limited to a center of the visual field image.

For example, the interested position may be controlled to be located at a specific position which is a predetermined distance away from the center of the visual field image.

Also, the interested position may be controlled to be located within a specific extent having a predetermined area rather than a specific one point. In this case, a system may be configured such that a control unit performs automatic driving only when the interested position moves outside the specific extent.

What is claimed is:

1. An endoscope system comprising:
   an insertion part elongated along a longitudinal axis, the insertion part having a bending portion capable of being bent relative to the longitudinal axis;
   an imaging device provided at a distal end portion of the insertion part;
   a joystick configured to operate bending of the bending portion;
   an actuator configured to generate a driving force used to drive the bending portion;
   a display monitor configured to display a visual field image acquired by the imaging device, and
   a controller configured to:
      control the actuator to drive the bending portion in a normal mode in accordance with an output from the joystick and to drive the bending portion in a lock-on mode that performs an automatic driving of the bending portion such that the imaging device faces a predetermined position irrespective of the output from the joystick, and
      during the lock-on mode, stop the automatic driving temporarily and allow the joystick to perform a resetting of the interested position when the output from the joystick exceeds a predetermined threshold value, and resume the automatic driving on the basis of the updated interested position when an output from the joystick satisfies a predetermined termination condition.

2. The endoscope system according to claim 1, wherein the controller is configured to drive the bending portion in accordance with the output from the joystick when the controller allows the resetting.

3. The endoscope system according to claim 1, wherein the controller is configured to display a cursor in the visual field image displayed on the display monitor and move the cursor in the visual field image in accordance with the output from the joystick when the controller allows the resetting.

4. The endoscope system according to claim 1, wherein the controller is configured to update the interested position when the output from the joystick satisfies the predetermined termination condition after the controller allows the resetting.

5. The endoscope system according to claim 1, wherein the joystick is configured to be capable of moving a position to be designated as the interested position in a depth direction of the visual field image during the resetting being allowed.

6. The endoscope system according to claim 1, wherein the actuator is a motor.

* * * * *